United States Patent
Hiraga et al.

(10) Patent No.: US 10,195,372 B2
(45) Date of Patent: Feb. 5, 2019

(54) PNEUMOPERITONEUM APPARATUS

(71) Applicant: OLYMPUS CORPORATION, Hachioji-shi, Tokyo (JP)

(72) Inventors: Kunitoshi Hiraga, Hino (JP); Takefumi Uesugi, Tachikawa (JP); Koji Yamaoka, Hamura (JP); Yuma Kasuya, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/211,842

(22) Filed: Jul. 15, 2016

(65) Prior Publication Data

US 2016/0325056 A1 Nov. 10, 2016

Related U.S. Application Data

(63) Continuation of application No. PCT/JP2015/057194, filed on Mar. 11, 2015.

(30) Foreign Application Priority Data

Aug. 27, 2014 (JP) .................. 2014-172989

(51) Int. Cl.
*A61M 13/00* (2006.01)
*A61B 17/34* (2006.01)
(Continued)

(52) U.S. Cl.
CPC ....... *A61M 13/003* (2013.01); *A61B 17/3474* (2013.01); *A61M 39/22* (2013.01);
(Continued)

(58) Field of Classification Search
CPC ............ A61M 16/0875; A61M 13/003; A61B 17/3423; A61B 17/3474; A61B 2018/0212
(Continued)

(56) References Cited

U.S. PATENT DOCUMENTS 4,676,774 A * 6/1987 Semm ................ A61M 13/003
600/560
4,874,362 A * 10/1989 Wiest ................ A61M 13/003
600/560
(Continued)

FOREIGN PATENT DOCUMENTS

JP H08-126606 A 5/1996
JP 2000-139828 A 5/2000
(Continued)

OTHER PUBLICATIONS

Jan. 19, 2016 Search Report issued in Japanese Patent Application No. 2015-551294.
(Continued)

*Primary Examiner* — May Abouelela
(74) *Attorney, Agent, or Firm* — Oliff PLC

(57) ABSTRACT

A pneumoperitoneum apparatus includes: a gas feeding conduit; a gas feeding flow rate variable section; a first pressure measurement section coupled with the gas feeding conduit; a conduit for pressure measurement; a conduit for pressure measurement coupling part coupled with the conduit for pressure measurement; a second pressure measurement section coupled with the conduit for pressure measurement coupling part, and configured to measure pressure in the conduit for pressure measurement; a gas leaking part configured to communicate the gas in the conduit for pressure measurement to an outside to leak the gas in the conduit by a predetermined leakage; and a control section configured to determine that the conduit for pressure measurement is crushed when pressure measured by the second pressure measurement section is smaller than a predetermined threshold.

11 Claims, 10 Drawing Sheets

(51) Int. Cl.
  *A61M 39/22* (2006.01)
  *A61M 16/00* (2006.01)
(52) U.S. Cl.
  CPC ... *A61M 39/227* (2013.01); *A61M 2016/0027* (2013.01); *A61M 2016/0033* (2013.01); *A61M 2039/226* (2013.01); *A61M 2202/0225* (2013.01); *A61M 2205/3341* (2013.01); *A61M 2205/3344* (2013.01); *A61M 2205/3379* (2013.01); *A61M 2205/7545* (2013.01); *A61M 2205/7563* (2013.01)
(58) Field of Classification Search
  USPC .......................................... 600/560; 604/26
  See application file for complete search history.

(56) References Cited

U.S. PATENT DOCUMENTS

| | | | | |
|---|---|---|---|---|
| 5,006,109 | A * | 4/1991 | Douglas | A61M 13/003 600/560 |
| 5,013,294 | A * | 5/1991 | Baier | A61M 13/003 600/560 |
| 5,152,745 | A * | 10/1992 | Steiner | A61M 13/003 141/197 |
| 5,328,458 | A * | 7/1994 | Sekino | A61M 13/003 604/23 |
| 5,360,396 | A * | 11/1994 | Chan | A61M 13/003 600/560 |
| 5,423,741 | A * | 6/1995 | Frank | A61M 13/003 604/23 |
| 6,042,573 | A | 3/2000 | Lucey | |
| 6,206,878 | B1 * | 3/2001 | Bishop | A61B 18/042 219/121.55 |
| 6,299,592 | B1 | 10/2001 | Zander | |
| 6,402,714 | B1 * | 6/2002 | Kraft-Kivikoski | A61M 13/003 600/560 |
| 6,554,780 | B1 * | 4/2003 | Sampson | A61B 18/00 600/560 |
| 7,569,027 | B2 * | 8/2009 | Uesugi | A61M 13/003 604/23 |
| 7,722,559 | B2 * | 5/2010 | Uesugi | A61M 13/003 600/560 |
| 7,981,072 | B2 * | 7/2011 | Uesugi | A61M 13/003 600/560 |
| 8,366,654 | B2 * | 2/2013 | Iranitalab | A61L 2/10 604/26 |
| 8,702,620 | B2 * | 4/2014 | Gefen | A61B 1/00082 600/481 |
| 8,734,381 | B2 * | 5/2014 | Noda | A61M 13/003 604/23 |
| 8,840,580 | B2 * | 9/2014 | Uesugi | A61B 50/13 600/560 |
| 8,926,587 | B2 * | 1/2015 | Faif | A61M 13/003 600/560 |
| 9,017,279 | B2 * | 4/2015 | Iranitalab | A61M 13/003 604/26 |
| 2005/0222535 | A1 * | 10/2005 | Uesugi | A61B 1/00039 604/26 |
| 2007/0255165 | A1 * | 11/2007 | Uesugi | A61B 1/00135 600/560 |
| 2013/0014593 | A1 | 1/2013 | Tabaru et al. | |
| 2014/0236074 | A1 * | 8/2014 | Faif | A61M 16/1075 604/26 |

FOREIGN PATENT DOCUMENTS

| | | |
|---|---|---|
| JP | 2002-508195 A | 3/2002 |
| JP | 2013-024574 A | 2/2013 |
| WO | 99/29250 A1 | 6/1999 |

OTHER PUBLICATIONS

May 17, 2016 Office Action issued in Japanese Patent Application No. 2015-551294.

Jun. 9, 2015 Search Report issued in International Patent Application No. PCT/JP2015/057194.

* cited by examiner

PNEUMOPERITONEUM APPARATUS

CROSS REFERENCE TO RELATED APPLICATION

This application is a continuation application of PCT/JP2015/057194 filed on Mar. 11, 2015 and claims benefit of Japanese Application No. 2014-172989 filed in Japan on Aug. 27, 2014, the entire contents of which are incorporated herein by this reference.

BACKGROUND OF THE INVENTION

1. Field of the Invention

An embodiment of the present invention relates to a pneumoperitoneum apparatus, in particular, to a pneumoperitoneum apparatus that measures pressure in a body cavity in real time through a dedicated tube for pressure measurement that is coupled with the cavity.

2. Description of the Related Art

In recent years, to suppress invasion into a patient, a laparoscopic surgical operation is performed in which therapeutic treatment is performed without an abdominal operation. In the laparoscopic surgical operation, for example, a first trocar that guides an observation endoscope into a body cavity, and a second trocar that guides treatment instruments to a treated site are pierced into an abdomen of the patient. In the laparoscopic surgical operation, treatment, etc. is performed while the treated site and the treatment instruments that are inserted into the body cavity through an insertion hole of the second trocar are observed with use of the endoscope that is inserted into the body cavity through an insertion hole of the first trocar.

In such a laparoscopic surgical operation, a pneumoperitoneum apparatus is used in order to secure a visual field of the endoscope and to secure a region in which the treatment instruments are operated. The pneumoperitoneum apparatus injects, for example, carbon dioxide as pneumoperitoneum gas into the body cavity to expand the cavity at a predetermined pressure, thereby securing the visual field of the endoscope and the operation region of the treatment instruments.

Typically, the pneumoperitoneum apparatus uses a gas feeding tube that feeds gas into the cavity, to measure pressure in the cavity. Therefore, the pneumoperitoneum apparatus temporarily stops the gas feeding and then measures the pressure in the cavity, after feeding the gas into the cavity for a predetermined time period. Further, the pneumoperitoneum apparatus performs such intermittent gas feeding until the pressure in the cavity reaches a set pressure (for example, refer to Japanese Patent Application Laid-Open Publication No. 8-126606).

An apparatus disclosed in U.S. Pat. No. 6,299,592 detects crushing of an RTPS tube with use of the fact that, in a case where a small amount of gas is fed to the RTPS tube, excess pressure is applied to an inside of the tube when the tube is crushed.

SUMMARY OF THE INVENTION

A pneumoperitoneum apparatus according to an aspect of the present invention includes: a gas feeding conduit communicated with a gas feeding source that feeds a predetermined gas, to supply the gas to a body cavity of a patient; a gas feeding flow rate variable section configured to regulate a flow rate of the gas that is supplied to the gas feeding conduit; a first pressure measurement section coupled with the gas feeding conduit; a conduit for pressure measurement used to measure pressure in the body cavity of the patient; a conduit for pressure measurement coupling part coupled with the conduit for pressure measurement; a second pressure measurement section coupled with the conduit for pressure measurement coupling part through a relay conduit, and configured to measure pressure in the conduit for pressure measurement; a gas leaking part provided between the conduit for pressure measurement and the relay conduit, and configured to communicate the gas in the conduit for pressure measurement to an outside to leak the gas in the conduit by a predetermined leakage; and a control section configured to determine that the conduit for pressure measurement is crushed when pressure measured by the second pressure measurement section is smaller than a predetermined threshold.

DETAILED DESCRIPTION OF THE PREFERRED EMBODIMENTS

In the following, embodiments are described with reference to drawings.

First Embodiment

Figure 1:
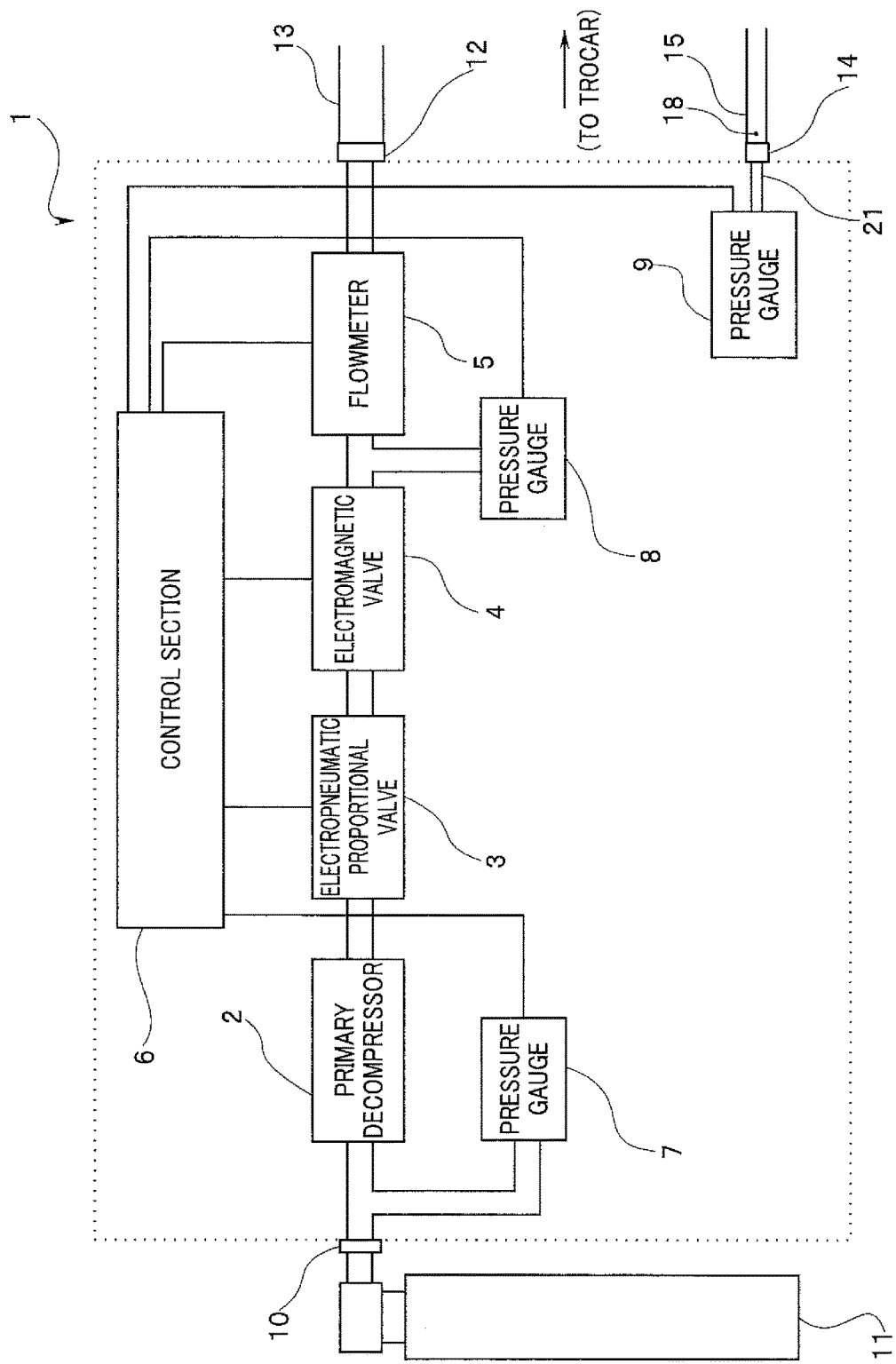
FIG. 1 is a diagram illustrating an example of an entire configuration of a pneumoperitoneum apparatus 1 according to a first embodiment of the present invention.

FIG. 1 is a diagram illustrating an example of an entire configuration of a pneumoperitoneum apparatus 1 according to a first embodiment of the present invention. As illustrated in FIG. 1, the pneumoperitoneum apparatus 1 according to the present embodiment mainly includes: a primary decompressor 2; an electropneumatic proportional valve 3; an electromagnetic valve 4 that opens or closes a gas feeding conduit; a flowmeter 5 that measures a flow rate of a gas to be fed; a pressure gauge 7 that measures supplying pressure of the gas to be fed; pressure gauges 8 and 9 that each measure pressure in a body cavity; and a control section 6 that controls respective components in the pneumoperitoneum apparatus 1.

Also, the pneumoperitoneum apparatus 1 is provided with a gas feeding pipe sleeve 12, an RTPS pipe sleeve 14, and a cylinder pipe sleeve 10. The cylinder pipe sleeve 10 is coupled with a carbon dioxide cylinder 11 serving as a gas feeding source through a high-pressure gas tube. The gas feeding pipe sleeve 12 is coupled with a gas feeding tube 13 serving as the gas feeding conduit to feed pneumoperitoneum gas such as carbon dioxide into the body cavity through an unillustrated trocar that is inserted into a cavity. Also, the RTPS pipe sleeve 14 serving as a conduit for pressure measurement coupling part is coupled with an RTPS tube 15 serving as a conduit for pressure measurement to measure pressure in the body cavity through an unillustrated trocar that is inserted into the cavity.

The pressure gauge 7 measures pressure of carbon dioxide supplied from the carbon dioxide cylinder 11, and provides the measurement result to the control section 6. The primary decompressor 2 decompresses, to a predetermined pressure, high-pressure carbon dioxide supplied through the cylinder pipe sleeve 10. The electropneumatic proportional valve 3 serving as a gas feeding flow rate variable section is configured to vary force of a decompression spring that acts on a valve part, thereby electrically regulating pressure to the predetermined pressure. The electropneumatic proportional valve 3 varies pressure of the carbon dioxide that has been decompressed by the primary decompressor 2, to gas feeding pressure within a range from about 0 mmHg to about 100 mmHg, based on a control signal provided from the control section 6.

A gas feeding conduit on downstream side of the electropneumatic proportional valve 3 is configured of the electromagnetic valve 4, the pressure gauge 8, the flowmeter 5, the gas feeding pipe sleeve 12, and the gas feeding tube 13. In contrast, the pneumoperitoneum apparatus 1 further includes a conduit for body cavity pressure measurement in addition to the gas feeding conduit. The conduit for body cavity pressure measurement is configured of the pressure gauge 9, a relay conduit 21, the RTPS pipe sleeve 14, and the RTPS tube 15, and is used to measure pressure in the body cavity.

The electromagnetic valve 4 performs open/close operation, based on the control signal provided from the control section 6. The pressure gauge 8 serving as a first pressure measurement section measures pressure in the body cavity through the gas feeding tube 13, and provides the measurement result to the control section 6. The flowmeter 5 measures a flow rate of carbon dioxide supplied into the body cavity, and provides the measurement result to the control section 6. The pressure gauge 9 serving as a second pressure measurement section measures pressure in the body cavity through the RTPS tube 15, and provides the measurement result to the control section 6. The RTPS tube 15 is provided with a small hole 18 serving as a gas leaking part that allows the gas in the conduit to be leaked to outside of the conduit.

Note that, to rapidly detect crushing of the RTPS tube 15, a conduit capacity of the conduit for body cavity pressure measurement may be desirably small. Thus, each of the relay conduit 21 and the RTPS tube 15 has an inner diameter smaller than an inner diameter of the gas feeding tube 13. For example, when the inner diameter of the gas feeding tube 13 is about 6 mm to about 8 mm, each of the relay conduit 21 and the RTPS tube 15 may desirably have an inner diameter of about 1 mm to about 2 mm.

Figure 2:
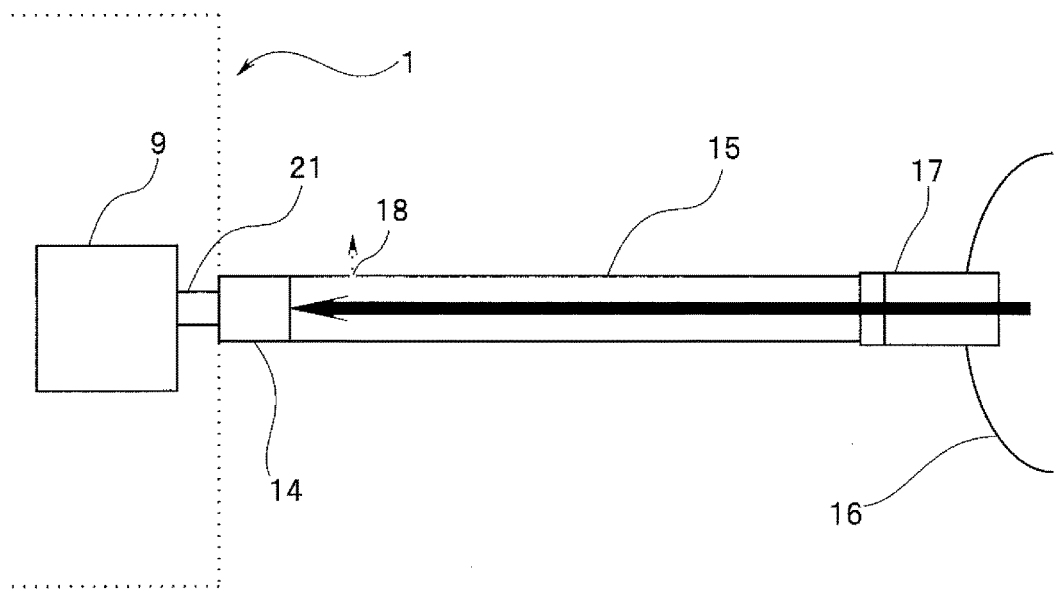
FIG. 2 is a diagram illustrating an example of a detailed configuration of a conduit for body cavity pressure measurement according to a first embodiment.

Next, the configuration of the conduit for body cavity pressure measurement is described with reference to FIG. 2. FIG. 2 is a diagram illustrating an example of a detailed configuration of the conduit for body cavity pressure measurement according to the first embodiment.

As illustrated in FIG. 2, the conduit for body cavity pressure measurement is provided across the inside of the pneumoperitoneum apparatus 1 and the outside of the pneumoperitoneum apparatus 1. The pressure gauge 9 is coupled with the RTPS pipe sleeve 14 through the relay conduit 21, inside the pneumoperitoneum apparatus 1. The RTPS tube 15 coupled with the RTPS pipe sleeve 14 is inserted into a body cavity of a patient 16 through the trocar 17, outside the pneumoperitoneum apparatus 1. Also, the RIPS tube 15 is provided with the small hole 18 near a terminal of the RTPS tube 15 on the pneumoperitoneum apparatus 1 side. The small hole 18 may be provided at an optional position on the RTPS tube 15; however, crushing of the tube is detected only when the crushing occurs on side closer to the trocar 17 than the small hole 18. Therefore, the small hole 18 may be desirably provided at a position as close as possible to the terminal of the RTPS tube 15 on the pneumoperitoneum apparatus 1 side.

The pressure in the body cavity is measured by the pressure gauge 9 in the pneumoperitoneum apparatus 1, through the trocar 17 and the RIPS tube 15. In a normal state in which crushing does not occur on the RTPS tube 15, a small amount of gas is leaked from the small hole 18 provided on the RTPS tube 15. The leakage is extremely small as compared with the total capacity of the body cavity, the trocar 17, the RTPS tube 15, and the relay conduit 21 that are filled with the gas.

For example, a case is examined in which the total capacity of the body cavity and the trocar is 3 L, a length of the RTPS tube 15 is 3 m, a diameter (an inner diameter) of each of the RTPS tube 15 and the relay conduit 21 is 2 mm, and the length of the relay conduit 21 is 10 cm. In this case, the capacity of the conduit for body cavity pressure measurement and the body cavity is calculated from the following equation (1).

$$3+(1\times1\times3.14\times3100)/1000000 = 3.009734\ [L] \qquad (1)$$

When the leakage of the gas from the small hole 18 is, for example, about 1 mL/Sec to about 2 mL/Sec, the leakage with respect to the capacity of the part that is filled with the gas becomes about 0.03% to about 0.06%. Thus, the reduction of the pressure in the body cavity due to the leakage of the gas from the small hole 18 is ignorable, and the pressure measured by the pressure gauge 9 may be accordingly considered to be coincident with the pressure in the body cavity. In this way, the conduit for body cavity pressure measurement is configured as illustrated in FIG. 2, which makes it possible to measure the pressure in the body cavity through the RTPS tube 15 in real time while continuously performing gas feeding without temporarily stopping the gas feeding to measure the pressure in the body cavity.

Figure 3:
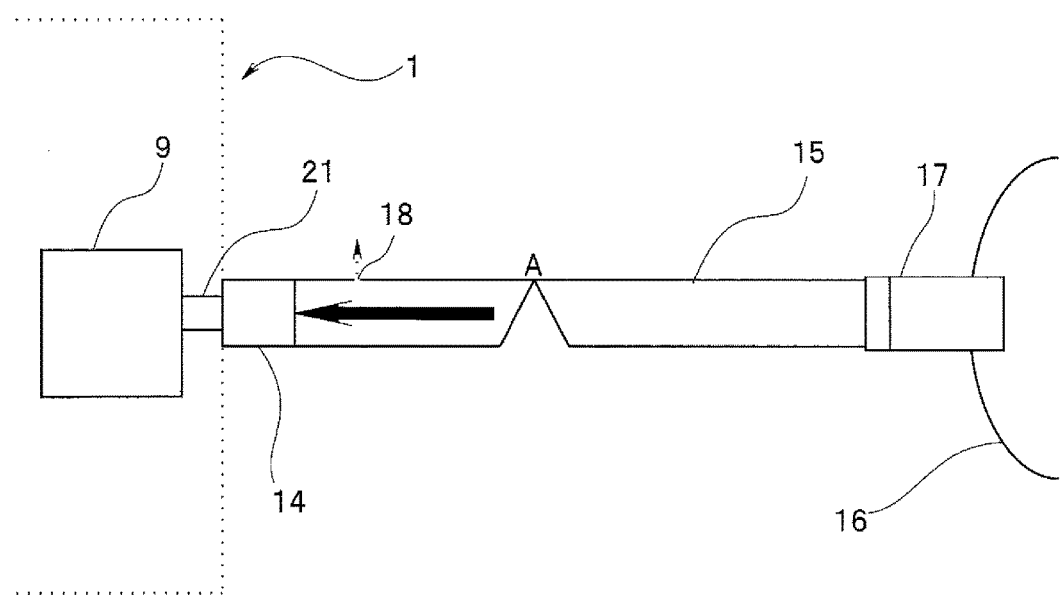
FIG. 3 is a diagram illustrating a state in which an RTPS tube 15 is crushed.

Next, a case in which crushing occurs on the RTPS tube 15 is described. FIG. 3 is a diagram illustrating a state in which the RTPS tube 15 is crushed. As illustrated in FIG. 3, when crushing occurs at a point A in the middle of the RTPS tube 15, a small amount of gas in the conduit is leaked from the small hole 18, as with the case in which the crushing does not occur. However, the capacity of the conduit filled with the gas, namely, a combined capacity of the capacity of the relay conduit 21 and a partial capacity of the RTPS tube 15 from the RTPS pipe sleeve 14 to the crushed part A is extremely smaller than that in the case in which the crushing does not occur. For example, a case is examined in which a length of the RTPS tube 15 from an end part of the RTPS tube 15 on the pneumoperitoneum apparatus 1 side to the point A is 1 m, the diameter (the inner diameter) of each of the RTPS tube 15 and the relay conduit 21 is 2 mm, and the length of the relay conduit 21 is 10 cm. In this case, the capacity of the conduit for body cavity pressure measurement from the pressure gauge 9 to the point A is calculated from the following equation (2).

$$(1\times1\times3.14\times1100)/1000000=0.003454\ [L] \quad (2)$$

As mentioned above, in the case where the crushing occurs, even when the leakage of the gas from the small hole 18 is extremely small, for example, about 1 mL/Sec to about 2 mL/Sec, the pressure in the conduit is decreased to atmospheric pressure in about 1.5 seconds to about 4 seconds after the crushing occurs because the capacity of the conduit for body cavity pressure measurement is smaller than the capacity of the body cavity. Therefore, monitoring the pressure gauge 9 to detect the decrease of the measurement value makes it possible to detect crushing of the RTPS tube 15.

Note that the specific numerals used in the above-described example are merely examples, and the inner diameters and the lengths of the RTPS tube 15 and the relay conduit 21 may be modified to appropriate sizes.

Figure 4:
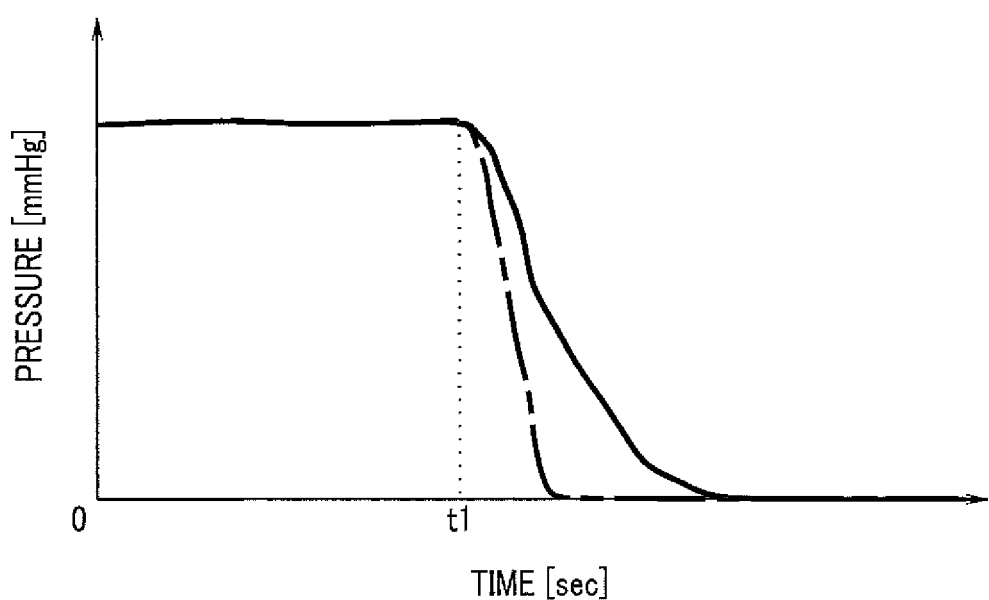
FIG. 4 is a diagram illustrating variation of a measurement value of a pressure gauge 9 in a state in which the RTPS tube 15 is crushed.

FIG. 4 is a diagram illustrating variation of the measurement value of the pressure gauge 9 in the case in which the RTPS tube 15 is crushed. A vertical axis indicates the measurement value of the pressure gauge 9, and a horizontal axis indicates time. In FIG. 4, a solid line indicates an example of pressure variation when the RTPS tube 15 is crushed, and an alternate long and short dash line indicates an example of pressure variation when the RTPS tube 15 is come off. When the RTPS tube 15 is crushed at time t1, the measurement value of the pressure gauge 9 is decreased without delay, and shortly after, reaches the atmospheric pressure (0 mmHg). Monitoring the variation of the measurement value of the pressure gauge 9 as mentioned above makes it possible to find out the crushing of the RTPS tube 15.

Note that, when the RTPS tube 15 is come off at the same time t1, the measurement value of the pressure gauge 9 is decreased more drastically than the crushed case, and reaches the atmospheric pressure (0 mmHg) immediately. Therefore, it is possible to determine whether the RTPS tube 15 is crushed or come off based on the decreasing degree (a gradient) of the measurement value of the pressure gauge 9, which allows for rapid restoration to the normal state.

Figure 5:
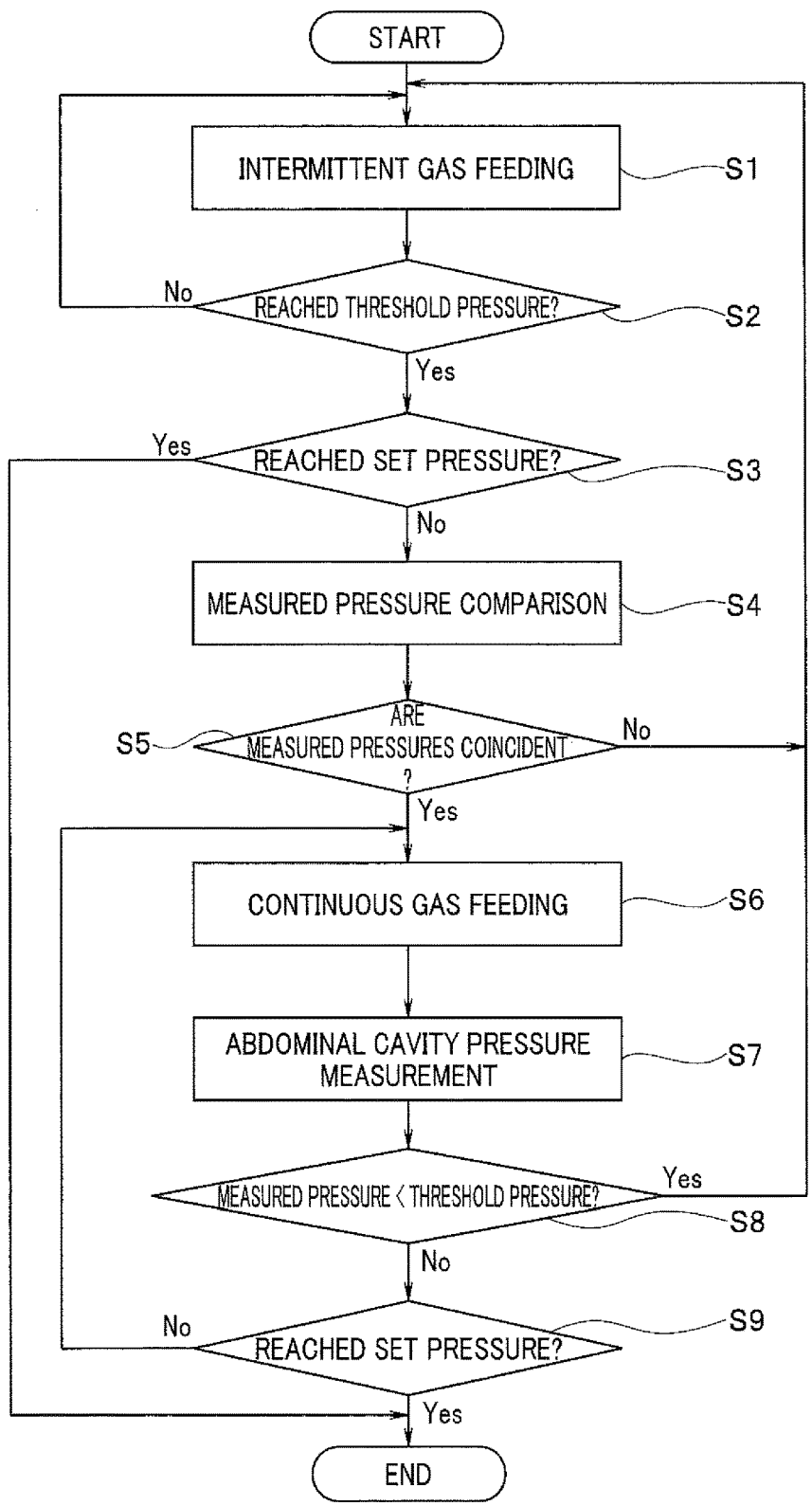
FIG. 5 is a flowchart illustrating an example of a gas feeding operation procedure by the pneumoperitoneum apparatus 1.

Next, a procedure of feeding gas into the body cavity of the patient to perform pneumoperitoneum with use of the pneumoperitoneum apparatus 1 according to the present embodiment is described with reference to FIG. 5. FIG. 5 is a flowchart illustrating an example of a gas feeding operation procedure by the pneumoperitoneum apparatus 1.

First, a series of steps from step S1 to step S5 are executed to determine whether the pneumoperitoneum apparatus 1 is correctly coupled with the body cavity of the patient through the RTPS tube 15. To determine the coupling of the RTPS tube 15, a method of comparing the measurement value of the pressure gauge 8 with the measurement value of the pressure gauge 9 is used. When the RTPS tube 15 is not correctly coupled (including a case in which the RTPS tube 15 is bent), difference occurs between the measurement value of the pressure gauge 8 and the measurement value of the pressure gauge 9. Therefore, it is determined that the RTPS tube 15 is correctly coupled when the measurement value of the pressure gauge 8 is coincident with the measurement value of the pressure gauge 9.

To compare the measurement value of the pressure gauge 8 with the measurement value of the pressure gauge 9, however, it is necessary for the body cavity to be expanded to some extent. This is because, when the comparison of the pressure between the pressure gauges is made at the body cavity pressure of 0 mmHg, it is difficult to determine whether the body cavity is really vacant, or the RTPS tube 15, is come off and the atmospheric pressure is thus actually measured, which may result in incorrect determination. Therefore, as with an existing pneumoperitoneum apparatus, the control section 6 first controls the electropneumatic proportional valve 3 to alternately perform the gas feeding and stop of the gas feeding, thereby performing intermittent gas feeding (step S1). The pressure in the body cavity is measured by the pressure gauge 8 during a period in which the gas feeding is stopped in the intermittent gas feeding. When the measurement value has not reached a predetermined threshold (No in step S2), the process returns to step S1 and the intermittent gas feeding is continued.

On the other hand, when the measurement value of the pressure gauge 8 has reached the predetermined threshold (Yes in step S2), the measurement value of the pressure gauge 8 is compared with target pressure (a set value) of the pneumoperitoneum. When the measurement value of the pressure gauge 8 has reached the set value (Yes in step S3), the pneumoperitoneum is sufficiently performed only through the intermittent gas feeding. Thus, the process does not make a transition to continuous gas feeding, and the gas feeding operation is terminated.

When the measurement value of the pressure gauge 8 has not reached the set value (No in step S3), the pressure in the body cavity is measured by the pressure gauge 9 through the RTPS tube 15. The measurement value of the pressure gauge 8 is compared with the measurement value of the pressure gauge 9 (step S4). When both measurement values have been coincident with each other (Yes in step S5), it is determined that the RTPS tube 15 is correctly coupled. On the other hand, when both measurement values have not been coincident with each other (No in step S5), it is determined that the RTPS tube 15 is not correctly coupled. Thus, the process returns to step S1, and the body cavity is subjected to pneumoperitoneum through the intermittent gas feeding.

When it is determined that the pneumoperitoneum apparatus 1 is correctly coupled with the body cavity of the patient through the RTPS tube 15 by the series of steps from step S1 to step S5, a series of steps from step S6 to step S9 is executed to perform pneumoperitoneum of the body cavity through the continuous gas feeding. The continuous gas feeding is a method of, while measuring the pressure in the body cavity in real time by the pressure gauge 9, continuously feeding gas into the body cavity based on the measurement result, thereby increasing the pressure in the body cavity to the set pressure at high speed. The pneumoperitoneum apparatus 1 according to the present embodiment has a feature to detect crushing of the RTPS tube 15 during the continuous gas feeding.

The feeding amount is regulated based on the measurement value of the pressure gauge 9 during the continuous gas feeding. Thus, if crushing occurs on the RTPS tube 15 to inhibit the pressure gauge 9 from correctly measuring the pressure in the body cavity, the gas may be excessively fed into the body cavity. Therefore, it is necessary to detect crushing of the RTPS tube 15 during the continuous gas feeding.

First, the control section 6 opens the electropneumatic proportional valve 3 and the electromagnetic valve 4 to perform the continuous gas feeding (step S6). The pressure gauge 9 measures the pressure in the body cavity at a predetermined timing during the continuous gas feeding (step S7). When crushing occurs on the RTPS tube 15, the measurement value of the pressure gauge 9 is decreased to the level of the atmospheric pressure shortly after the crushing occurs, because of the small hole 18 provided on the RTPS tube 15, in the pneumoperitoneum apparatus 1 according to the present embodiment. Therefore, it is possible to detect the crushing of the RTPS tube 15 by determining whether the measurement value obtained in step S7 is smaller than the predetermined threshold pressure (step S8).

When the measurement value of the pressure gauge 9 is smaller than the predetermined threshold pressure (Yes in step S8), it is determined that the RTPS tube 15 has been crushed, and the process returns to the intermittent gas feeding in step S1. Then, the intermittent gas feeding is continued without performing the continuous gas feeding until the crushing of the RTPS tube 15 is eliminated and the RTPS tube 15 is correctly coupled with the body cavity. Note that, when the crushing of the RTPS tube 15 is eliminated during the intermittent gas feeding, the measurement value of the pressure gauge 8 is coincident with the measurement value of the pressure gauge 9 in step S5. Thus, the process makes a transition to the continuous gas feeding in step S6 again.

On the other hand, when the measurement value of the pressure gauge 9 is equal to or greater than the predetermined threshold pressure (No in step S8), it is determined that crushing or other troubles do not occur on the RTPS tube 15 and the pressure in the body cavity is correctly measured. Subsequently, the measurement value of the pressure gauge 9 is compared with the target pressure (the set value) of the pneumoperitoneum. When the measurement value of the pressure gauge 9 has not reached the set value (No in step S9), the process returns to step S6, and the pneumoperitoneum by the continuous gas feeding is continued. When the measurement value of the pressure gauge 9 has reached the set value (Yes in step S9), the control section 6 controls the electropneumatic proportional valve 3 to close the valve 3, and the gas feeding operation is terminated.

As mentioned above, according to the present embodiment, since the RTPS tube 15 is provided with the small hole 18, the gas in the conduit for pressure measurement is leaked from the small hole 18 to outside of the conduit, which decreases the measurement value of the pressure gauge 9 to the level of the atmospheric pressure shortly after the crushing occurs on the RTPS tube 15. Thus, monitoring the measurement value of the pressure gauge 9 makes it possible to detect crushing of the RTPS tube 15, which eliminates the need for provision of a new expensive pneumatic member. Also, since it is unnecessary to perform the gas feeding, it is possible to perform pneumoperitoneum without excessively feeding gas into the body cavity.

Note that, in the above-described embodiment, the control section 6 controls the electropneumatic proportional valve 3 to open/close the gas feeding conduit. Alternatively, the control section 6 may control the electromagnetic valve 4 to open/close the gas feeding conduit. Also, in the above-described embodiment, the case has been exemplified in which one decompressor (the primary decompressor 2) that decreases the pressure of carbon dioxide to be fed is disposed in the gas feeding conduit. Alternatively, a plurality of decompressors may be provided to decrease the pressure of carbon dioxide in a stepwise manner.

Figure 6:
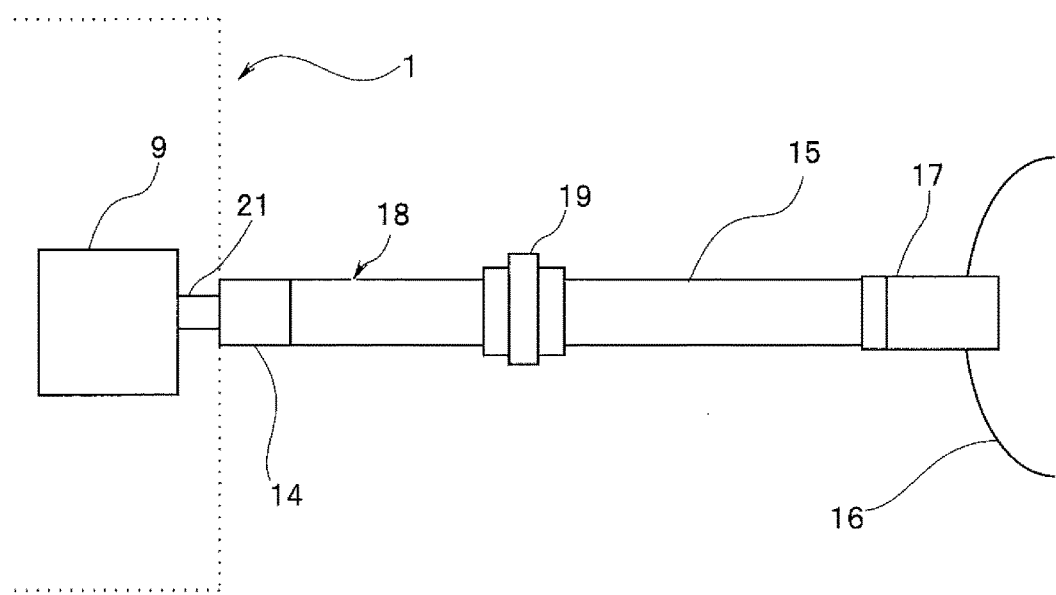
FIG. 6 is a diagram illustrating an example of a configuration of an RIPS tube 15 provided with a filter 19.

Further, as illustrated in FIG. 6, the pneumoperitoneum apparatus 1 may be configured to include a filter 19 disposed on the RTPS tube 15 to prevent the small hole 18 from being blocked by an impurity that is contained in the gas passing through the body cavity. FIG. 6 is a diagram illustrating an example of a configuration of the RTPS tube 15 provided with the filter 19. As illustrated in FIG. 6, the filter 19 capable of removing at least an impurity having a size larger than the diameter of the small hole 18 is provided on the RTPS tube 15 on side closer to the trocar 17 than the small hole 18. This makes it possible to prevent the small hole 18 from being blocked by the impurity, and to prevent impurity, and pathogen, a cell, etc. attached to the impurity from entering and contaminating the inside of the pneumoperitoneum apparatus 1.

Also, to prevent the RTPS tube 15 from being crushed, a part of the RTPS tube 15 except for both ends of the RTPS tube 15 and a part of the gas feeding tube 13 except for both ends of the gas feeding tube 13 may be integrally disposed through bonding. It is necessary to couple the both ends of the RTPS tube 15 with the RTPS pipe sleeve 14 and the trocar 17, and to couple the both ends of the gas feeding tube 13 with the gas feeding pipe sleeve 12 and a trocar other than the trocar 17. If the RTPS tube 15 and the gas feeding tube 13 are entirely bonded and integrated, these coupling is not performed. Therefore, both end parts of the RTPS tube 15 and the gas feeding tube 13 are not integrated and are independent from each other in order to be coupled with predetermined components.

When being integrated, the same force is applied to the gas feeding tube 13 and the RTPS tube 15 from the outside. In addition, the gas feeding tube 13 is formed to have a diameter larger than that of the RTPS tube 15. Typically, a minimum bending radius (a minimum radius enabling the tube to maintain a conduit shape without crushing when bending force is applied) is increased as the diameter is larger. Therefore, the gas feeding tube 13 having the large diameter is crushed before the RTPS tube 15 at a part at which the gas feeding tube 13 and the RTPS tube 15 are integrated, when the bending force is applied thereto from the outside. The crushing of the gas feeding tube 13 is detected by the pressure gauge 8 as with an existing pneumoperitoneum apparatus. This makes it possible to avoid a state in which crushing tends to occur, before the RTPS tube 15 is crushed.

Also, if crushing force is applied, from the outside, to the part where the gas feeding tube 13 and the RTPS tube 15 are integrated, for example, in a case in which the tube laid on a floor is trampled, the gas feeding tube 13 having the large diameter is crushed before the RTPS tube 15. Therefore, bonding and integrating the gas feeding tube 13 and the RTPS tube 15 makes it possible to suppress crushing of the RTPS tube 15 having the small diameter. Also, monitoring the pressure gauge 8 to detect the crushing of the gas feeding tube 13 makes it possible to promptly detect the state in which crushing tends to occur on the RTPS tube 15, which makes it possible to perform pneumoperitoneum operation more safely without crushing of the RTPS tube 15.

Second Embodiment

Figure 7:
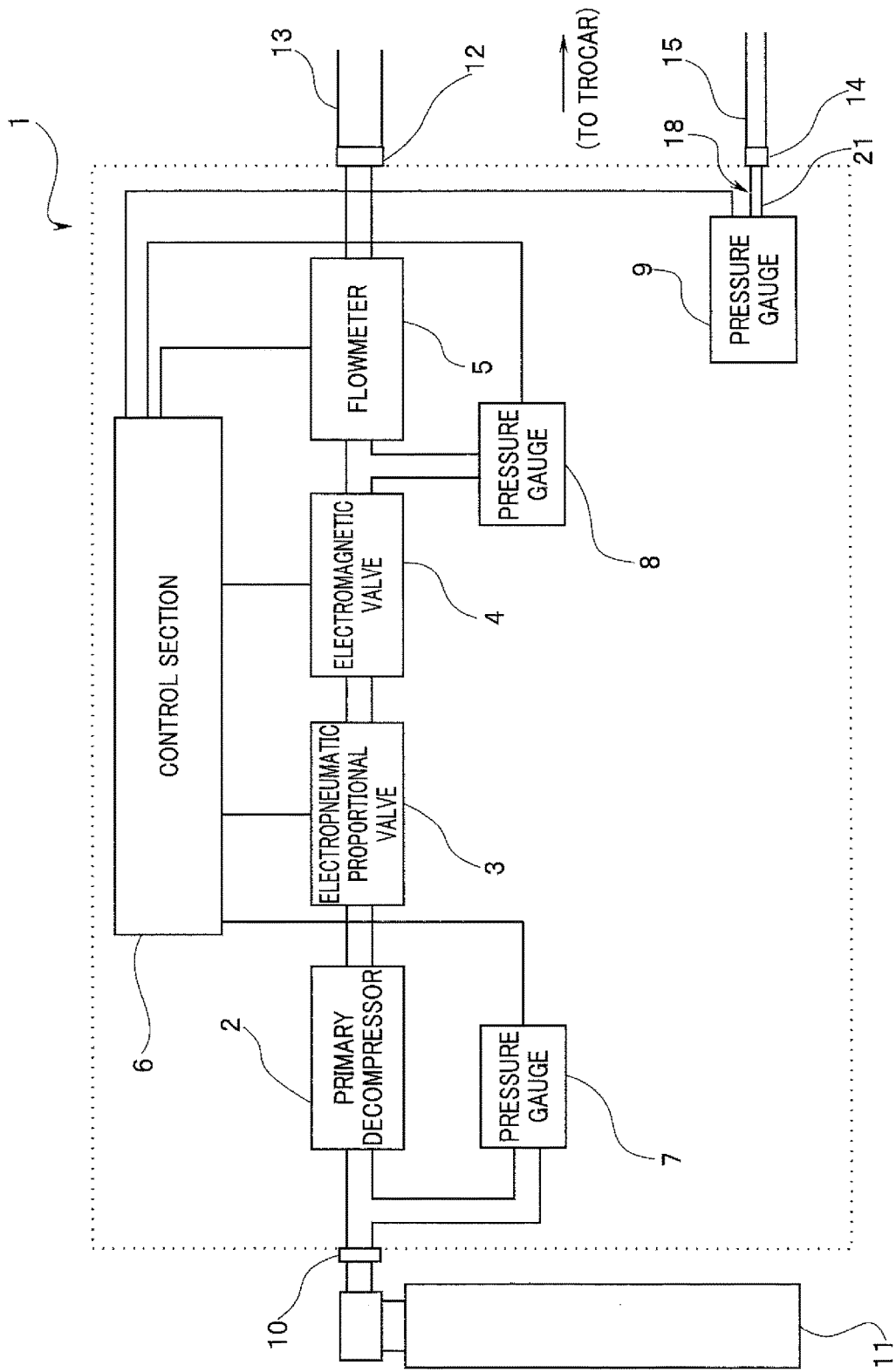
FIG. 7 is a diagram illustrating an example of an entire configuration of a pneumoperitoneum apparatus 1 according to a second embodiment.

In the pneumoperitoneum apparatus according to the first embodiment mentioned above, the small hole 18 that allows the gas in the conduit for body cavity pressure measurement to be leaked to the outside of the conduit, is provided on the RTPS tube 15. In contrast, the present embodiment is different from the first embodiment in that the small hole 18 is provided on the relay conduit 21. FIG. 7 is a diagram illustrating an example of the entire configuration of the pneumoperitoneum apparatus 1 according to the second embodiment. The pneumoperitoneum apparatus according to the present embodiment has a configuration similar to that of the first embodiment except for a position at which the small hole 18 is provided. Also, a method of detecting crushing of the RTPS tube 15 and a method of performing pneumoperitoneum are similar to those in the first embodiment. In the pneumoperitoneum apparatus according to the first embodiment, when crushing occurs on the RTPS tube 15 between the small hole 18 and the RTPS pipe sleeve 14, it is not possible to detect the crushing by the pressure gauge 9. In contrast, in the pneumoperitoneum apparatus according to the present embodiment, since the small hole 18 is provided on the relay conduit 21, it is possible to detect crushing surely irrespective of the position of the crushing.

In this way, in the present embodiment, providing the small hole 18 on the relay conduit 21 in the pneumoperitoneum apparatus 1 makes it possible to surely detect crushing when the crushing occurs on any position of the RTPS tube 15. Therefore, it is possible to surely prevent wrong measurement of the pressure in the body cavity by the pressure gauge 9, and to accordingly perform pneumoperitoneum safely.

Note that, also in the present embodiment, the pneumoperitoneum apparatus 1 may be configured to include the filter 19 disposed on the RTPS tube 15 to prevent the small hole 18 from being blocked by an impurity that is contained in the gas passing through the body cavity. Also, to prevent the RTPS tube 15 from being crushed, a part of the RTPS tube 15 except for both ends of the RTPS tube 15 and a part of the gas feeding tube 13 except for both ends of the gas feeding tube 13 may be integrally disposed through bonding.

Third Embodiment

Figure 8:
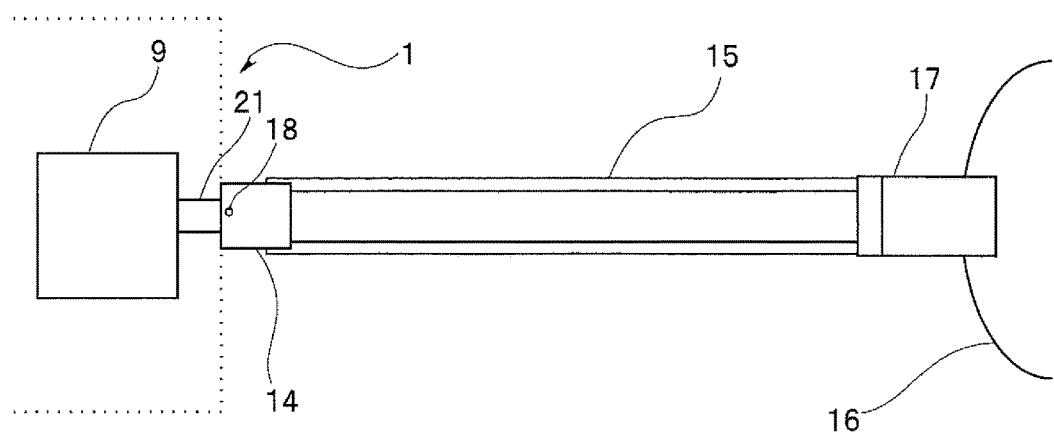
FIG. 8 is a diagram illustrating an example of a detailed configuration of a conduit for body cavity pressure measurement according to a third embodiment.

In the pneumoperitoneum apparatus according to the first embodiment and the pneumoperitoneum apparatus according to the second embodiment mentioned above, the small hole 18 that allows the gas in the conduit for body cavity pressure measurement to be leaked to the outside of the conduit is provided on the RTPS tube 15 or on the relay conduit 21. In contrast, the present embodiment is different from the above-described embodiments in that the small hole 18 is provided in the RTPS pipe sleeve 14. FIG. 8 is a diagram illustrating an example of a detailed configuration of a conduit for body cavity pressure measurement according to a third embodiment. The pneumoperitoneum apparatus according to the present embodiment has a configuration similar to that of the first embodiment except for a position at which the small hole 18 is provided. Also, a method of detecting crushing of the RTPS tube 15 and a method of performing pneumoperitoneum are similar to those of the first embodiment.

In the pneumoperitoneum apparatus according to the first embodiment, when crushing occurs on the RTPS tube 15 between the small hole 18 and the RTPS pipe sleeve 14, it is not possible to detect the crushing by the pressure gauge 9. In contrast, in the pneumoperitoneum apparatus according to the present embodiment, since the small hole 18 is provided on the RTPS pipe sleeve 14 as illustrated in FIG. 8, it is possible to detect crushing surely irrespective of a position of the crushing. Also, in the pneumoperitoneum apparatus according to the second embodiment, when any trouble such as clog occurs on the small hole 18, it is necessary to disassemble the pneumoperitoneum apparatus to cope with the trouble, which needs time and labor, because the small hole 18 is provided on the relay conduit 21 inside the pneumoperitoneum apparatus. In contrast, in the pneumoperitoneum apparatus according to the present embodiment, since the small hole 18 is provided on the RTPS pipe sleeve 14 that is so disposed as to project from the pneumoperitoneum apparatus, maintainability with respect to troubles such as clog of the small hole 18 is high.

Figure 9:
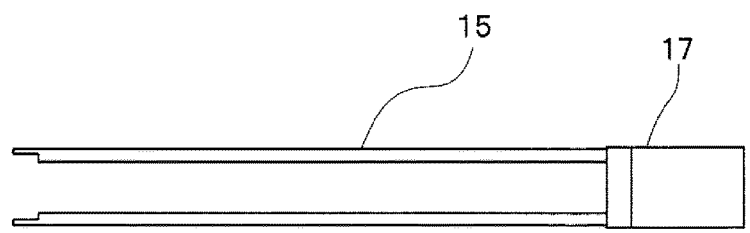
FIG. 9 is a diagram illustrating a detailed configuration of an RTPS tube 15 according to the third embodiment.

Note that, when the RTPS tube 15 is attached to the pneumoperitoneum apparatus 1, an outer circumference of an end part of the RTPS pipe sleeve 14 is typically covered with the end part of the RTPS tube 15, as illustrated in FIG. 8. At this time, there is a possibility that the RTPS tube 15 blocks the small hole 18 provided on the RTPS pipe sleeve 14 to inhibit the gas in the conduit from escaping through the small hole 18. Therefore, for example, as illustrated in FIG. 9, the end part (an end part on side attached to the RTPS pipe sleeve 14) of the RTPS tube 15 is made thin to form a distal end portion in a cutout shape. FIG. 9 is a diagram illustrating a detailed configuration of the RTPS tube 15 according to the third embodiment. At this time, the distal end of the RTPS tube 15 is so processed as to allow the length of the cutout part to be smaller than a length between the end part of the RTPS pipe sleeve 14 and the small hole 18.

When the RTPS tube 15 is attached to the RTPS pipe sleeve 14 as illustrated in FIG. 8, the cutout part provided on the distal end of the RTPS tube 15 functions as a stopper, thereby preventing the RTPS tube 15 from blocking the small hole 18 that is provided on the RTPS pipe sleeve 14.

Note that the method of preventing the RTPS tube 15 from blocking the small hole 18 provided on the RTPS pipe sleeve 14 is not limited to the method of providing the cutout part at the distal end portion of the RTPS tube 15 mentioned above. For example, a stopper or other means may be provided at a part closer to the end part attached with the RTPS tube 15 than the small hole 18 of the RTPS pipe sleeve 14.

As mentioned above, in the present embodiment, providing the small hole 18 on the RTPS pipe sleeve 14 makes it possible to surely detect crushing even when the crushing occurs on any part of the RTPS tube 15. Therefore, it is possible to surely prevent wrong measurement of the pressure in the body cavity by the pressure gauge 9, and to accordingly perform the pneumoperitoneum safely. Also, since the small hole 18 is provided on the RTPS pipe sleeve 14 that is so disposed as to project from the pneumoperitoneum apparatus, maintainability with respect to troubles such as clog of the small hole 18 is high.

Note that, also in the present embodiment, the pneumoperitoneum apparatus 1 may be configured to include the filter 19 disposed on the RTPS tube 15 to prevent the small hole 18 from being blocked by an impurity that is contained in the gas passing through the body cavity. Also, to prevent the RTPS tube 15 from being crushed, a part of the RTPS tube 15 except for both ends of the RTPS tube 15 and a part of the gas feeding tube 13 except for both ends of the gas feeding tube 13 may be integrally disposed through bonding.

Fourth Embodiment

In the above-described pneumoperitoneum apparatuses according to the respective first to third embodiments, the small hole 18 is provided on the conduit for pressure measurement, as a gas leaking part that allows the gas in the conduit for pressure measurement to be leaked to the outside of the conduit. In contrast, the present embodiment is different from the above-described embodiments in that a part of the conduit for pressure measurement is formed of a gas-permeable material. The pneumoperitoneum apparatus according to the present embodiment has a configuration similar to that of the first embodiment except that a part of the RTPS tube 15 is formed of a gas-permeable material, in place of the small hole 18. Also, a method of detecting crushing of the RTPS tube 15 and a method of performing pneumoperitoneum are similar to those of the first embodiment.

Figure 10:
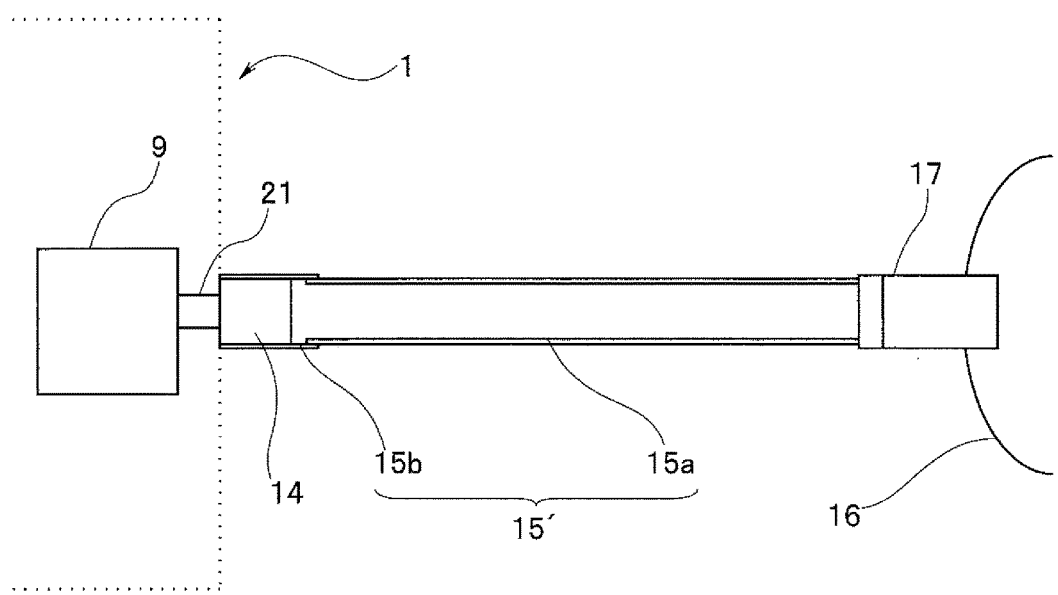
FIG. 10 is a diagram illustrating an example of a detailed configuration of a conduit for body cavity pressure measurement according to a fourth embodiment.

FIG. 10 is a diagram illustrating an example of a detailed configuration of a conduit for body cavity pressure measurement according to a fourth embodiment. An RTPS tube 15' according to the present embodiment is configured by fixing a tube 15b to an end part of a tube 15a. The tube 15a is formed of, for example, a gas non-permeable material such as vinyl chloride, and the tube 15b is formed of for example, a gas-permeable material such as silicon. Further, the tube 15b formed of the gas non-permeable material is attached to the RTPS pipe sleeve 14 to configure the conduit for pressure measurement. A leakage of the gas from the conduit for pressure measurement to the outside of the conduit depends on the material of the tube 15b and a length between an end part of the RTPS pipe sleeve 14 on the RTPS tube 15' side and a bonding end at which the tube 15a and the tube 15b are bonded.

If the leakage of the gas from the tube 15b to the outside of the conduit is excessively large, efficiency of pneumoperitoneum is deteriorated. Thus, the leakage may be desirably small. Therefore, for example, when silicon is used as the material of the tube 15b, each component may be desirably configured to allow the length between the end part of the RTPS pipe sleeve 14 on the RTPS tube 15' side and the bonding end at which the tube 15a and the tube 15b are bonded, to become about several millimeters.

In this way, in the present embodiment, a part of the RTPS tube 15' serving as the gas leaking part is formed of a gas-permeable material. This makes it possible to detect crushing of the RTPS tube 15' without providing the small hole 18 on the RTPS tube 15'. Note that the tube 15b may be desirably disposed on the end part of the RTPS tube 15' on the RTPS pipe sleeve 14 side. However, the position of the tube 15b is not limited thereto, and for example, the tube 15b may be disposed in the middle of the gas non-permeable tube 15a.

Fifth Embodiment

In the pneumoperitoneum apparatus according to the second embodiment mentioned above, the small hole 18 is provided on the relay conduit 21, as the gas leaking part that allows the gas in the conduit for pressure measurement to be leaked to the outside of the conduit. In contrast, the present embodiment is different from the second embodiment in that an opening/closing electromagnetic valve 20 is used in place of the small hole 18. A pneumoperitoneum apparatus 1' according to the present embodiment has a configuration similar to that of the second embodiment except that the small hole 18 is not formed on the relay conduit 21 and the opening/closing electromagnetic valve 20 is disposed as illustrated in FIG. 11.

Figure 11:
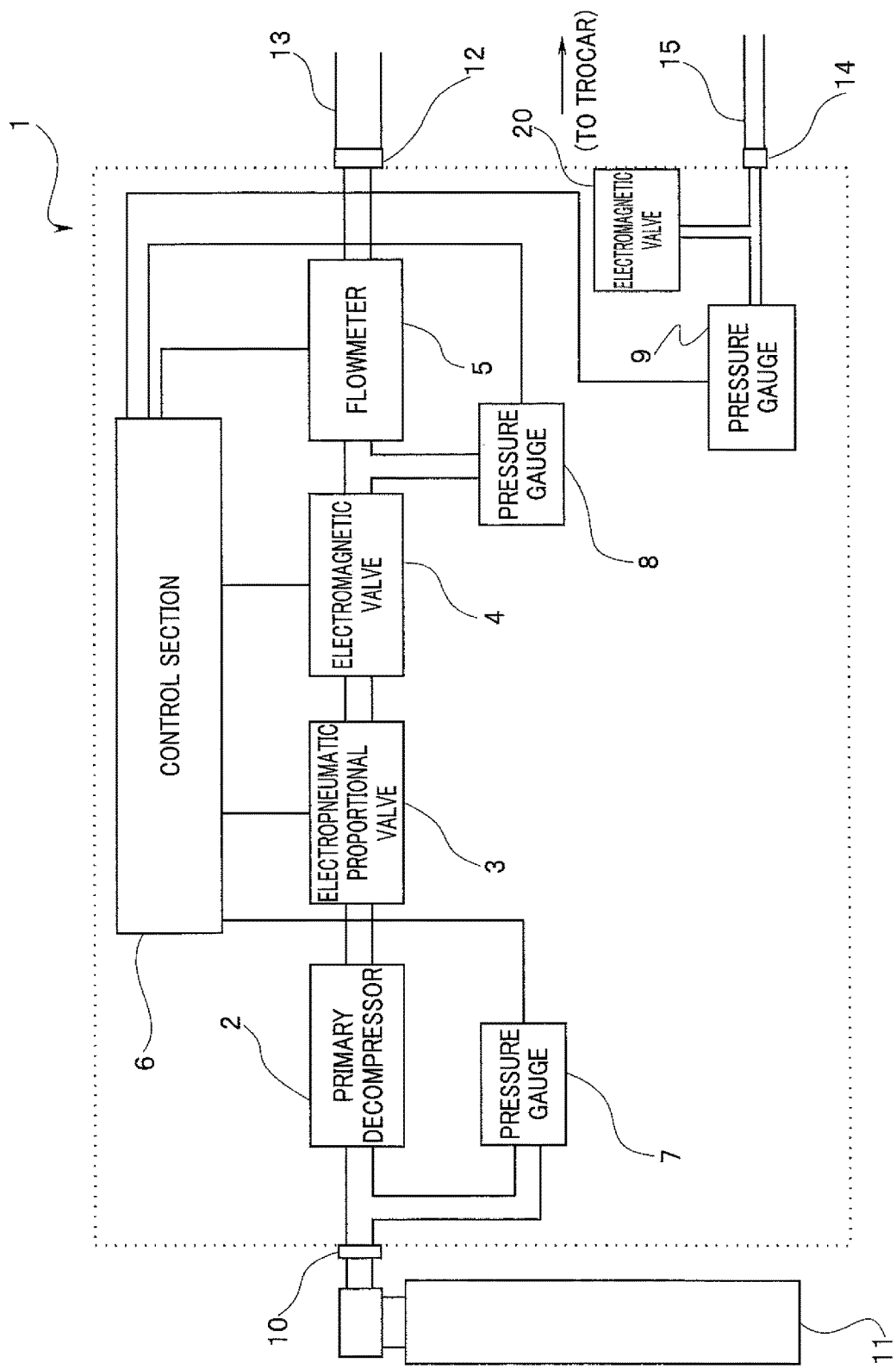
FIG. 11 is a diagram illustrating an example of an entire configuration of a pneumoperitoneum apparatus 1' according to a fifth embodiment.

FIG. 11 is a diagram illustrating an example of an entire configuration of the pneumoperitoneum apparatus 1' according to a fifth embodiment. The opening/closing electromagnetic valve 20 performs valve opening/closing operation in response to the control signal provided from the control section 6. In a case where the valve is opened, a small amount of gas is leaked to the outside of the relay conduit 21 through the valve. In other words, in the case where the opening/closing electromagnetic valve 20 is opened, the state is similar to the state in the case where the small hole 18 is provided on the relay conduit 21. On the other hand, when the opening/closing electromagnetic valve 20 is closed, intentional leakage of the gas from the conduit for pressure measurement including the relay conduit 21 is stopped. Note that the opening/closing electromagnetic valve 20 is adjusted to allow the leakage of the gas in the open state to be equivalent to the leakage (for example, about 1 mL/Sec to about 2 mL/Sec) in the case where the small hole 18 is provided on the relay conduit 21.

In other words, in the case where the opening/closing electromagnetic valve 20 is opened, when crushing occurs on the RTPS tube 15, the gas in the conduit for body cavity pressure measurement from the pressure gauge 9 up to the crushed point is leaked to the outside through the valve. Therefore, detecting the decrease of the measurement value of the pressure gauge 9 in the state in which the opening/closing electromagnetic valve 20 is opened makes it possible to detect crushing of the RTPS tube 15. In the case where the opening/closing electromagnetic valve 20 is closed, the crushing of the RTPS tube 15 cannot be detected; however, the gas in the conduit for body cavity pressure measurement is not leaked to the outside of the conduit, which makes it possible to perform pneumoperitoneum efficiently.

Figure 12:
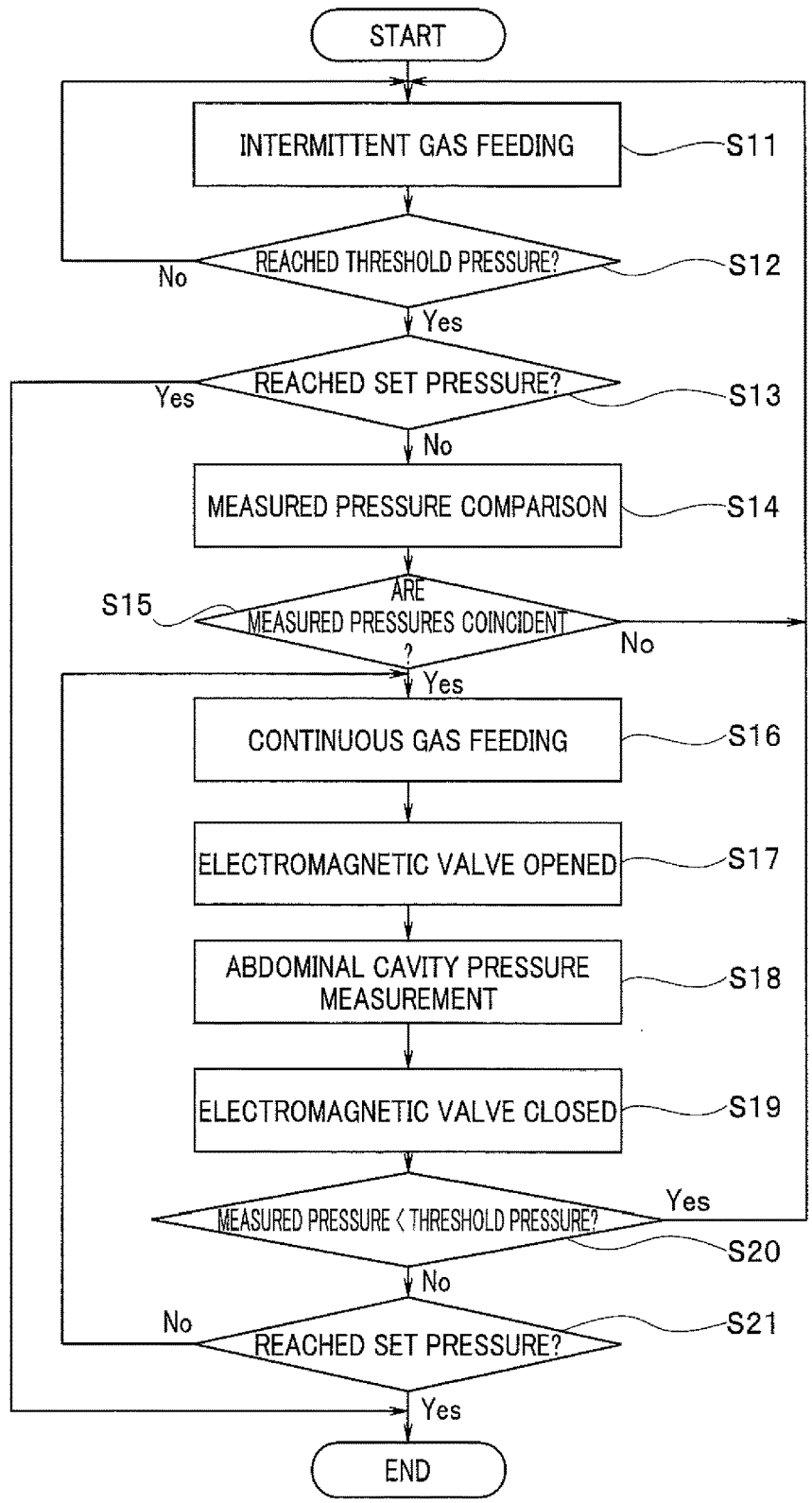
FIG. 12 is a flowchart illustrating an example of a gas feeding operation procedure in the pneumoperitoneum apparatus 1'.

A procedure of feeding gas into a body cavity of a patient to perform pneumoperitoneum with use of the pneumoperitoneum apparatus having such a configuration is described with reference to FIG. 12. FIG. 12 is a flowchart illustrating an example of a gas feeding operation procedure by the pneumoperitoneum apparatus 1'.

First, a series of steps from step S11 to step S15 is executed to determine whether the pneumoperitoneum apparatus 1' is correctly coupled with the body cavity of the patient through the RTPS tube 15. The steps from step S11 to step S15 are similar to the steps from step S1 to step S5 in the gas feeding operation procedure by the pneumoperitoneum apparatus 1 according to the first embodiment described with reference to FIG. 5.

When it is determined, through the series of steps from step S11 to step S15, that the pneumoperitoneum apparatus 1' has been correctly coupled with the body cavity of the patient through the RTPS tube 15, a series of steps from step S16 to step S21 is then executed to perform pneumoperitoneum on the body cavity through the continuous gas feeding.

First, the control section 6 opens the electropneumatic proportional valve 3 and the electromagnetic valve 4 to perform the continuous gas feeding (step S16). Then, the control section 6 opens the opening/closing electromagnetic valve 20 at a predetermined timing (step S17). When the opening/closing electromagnetic valve 20 is opened, a small amount of gas is leaked through the valve, which allows for detection of crushing of the RTPS tube 15. Subsequently, pressure in the body cavity is measured by the pressure gauge 9 (step S18). After the measurement, the control section 6 closes the opening/closing electromagnetic valve 20 in order to prevent gas leakage (step S19).

When crushing occurs on the tube, the measurement value of the pressure gauge 9 is decreased to the level of the atmospheric pressure shortly after the crushing occurs. Therefore, determining whether the measurement value obtained in step S18 is smaller than the predetermined threshold pressure (step S20) makes it possible to detect crushing of the RTPS tube 15. When the measurement value of the pressure gauge 9 is smaller than the predetermined threshold pressure (Yes in step S20), it is determined that the RTPS tube 15 is crushed, and the process accordingly returns to the intermittent gas feeding in step S11. Then, the intermittent gas feeding is continued without performing the continuous gas feeding until the crushing of the RTPS tube 15 is eliminated and the RTPS tube 15 is correctly coupled with the body cavity. Note that, when the crushing of the RTPS tube 15 is eliminated during the intermittent gas feeding, the measurement value of the pressure gauge 8 is coincident with the measurement value of the pressure gauge 9 in step S15. Thus, the process makes a transition to the continuous gas feeding in step S16 again.

On the other hand, when the measurement value of the pressure gauge 9 is equal to or greater than the predetermined threshold pressure (No in step S20), it is determined that crushing or other troubles do not occur on the RTPS tube 15 and the pressure in the body cavity is correctly measured. Subsequently, the measurement value of the pressure gauge 9 is compared with the target pressure (the set value) of the pneumoperitoneum. When the measurement value of the pressure gauge 9 has not reached the set value (No in step S21), the process returns to step S16, and pneumoperitoneum by the continuous gas feeding is continued. When the measurement value of the pressure gauge 9 has reached the set value (Yes in step S21), the control section 6 controls the electropneumatic proportional valve 3 to close the valve 3, and the gas feeding operation is terminated.

As mentioned above, in the present embodiment, the opening/closing electromagnetic valve 20 is provided in the relay conduit 21, as the gas leaking part. Controlling open or close of the opening/closing electromagnetic valve 20 at timing to detect crushing of the RTPS tube 15 makes it possible to detect the crushing of the RTPS tube 15 while performing the pneumoperitoneum efficiently. In other words, when the opening/closing electromagnetic valve 20 is opened, it is possible to detect crushing of the RTPS tube 15 based on the measurement value of the pressure gauge 9, as with the above-described first to fourth embodiments. When the opening/closing electromagnetic valve 20 is closed, it is possible to perform the pneumoperitoneum efficiently because the leakage of the gas is eliminated.

Respective "sections" in the present specification are concepts corresponding to the respective functions of the embodiments, and do not necessarily correspond one-to-one with specific hardware and software routines. Therefore, in the present specification, the embodiments have been described assuming virtual circuit blocks (sections) having the respective corresponding functions of the embodiments. Also, the respective steps in each of the procedures in the present embodiment may be modified in execution order, executed together with the other steps at a time, or executed in order different for each execution, unless contrary to the nature thereof. Further, all or some of respective steps in each of the procedures in the present embodiment may be realized by hardware.

Although some embodiments of the present invention have been described, these embodiments are merely examples, and do not intend to limit the scope of the invention. These novel embodiments may be implemented in other various modes, and abbreviations, substitutions, and alternations may be made without departing from the scope of the invention. These embodiments and the modifications thereof are within the scope of the invention and within the scope of the appended claims or the equivalents thereof.

According to the pneumoperitoneum apparatus of the present invention, it is possible to detect crushing of an RTPS tube without newly providing an expensive pneumatic member and performing gas feeding.

What is claimed is:

1. A pneumoperitoneum apparatus comprising:
   a gas feeding conduit including a first end configured to be coupled to a gas feeding source that feeds a predetermined gas and a second end configured to be inserted into a body cavity of a patient;
   a gas feeding flow rate valve configured to regulate a flow rate of the gas that passes through the gas feeding conduit;
   a first pressure measurement device coupled with the gas feeding conduit;
   a pressure measurement conduit which (1) is different from the gas feeding conduit and (2) includes a third end configured to be inserted into the body cavity of the patient and a fourth end coupled with a pressure measurement conduit coupling part;
   a second pressure measurement device coupled with the pressure measurement conduit coupling part by a relay conduit, and configured to measure pressure in the pressure measurement conduit to measure pressure in the body cavity of the patient;
   a gas release included in the pressure measurement conduit or the relay conduit, and configured to pass gas in the pressure measurement conduit to an outside of the pressure measurement conduit by a predetermined leakage while (1) the gas is flowing through the gas feeding flow rate valve and the gas feeding conduit and (2) the second pressure measurement device is measuring the pressure in the body cavity; and
   a controller in communication with the gas feeding flow rate valve, the first pressure measurement device and the second pressure measurement device and configured to determine that the pressure measurement conduit is crushed when the pressure measured by the second pressure measurement device is lower than a predetermined threshold.

2. The pneumoperitoneum apparatus according to claim 1, wherein the gas release is a hole.

3. The pneumoperitoneum apparatus according to claim 1, wherein the gas release is a tube formed of a material that has a property allowing the gas to pass through the material.

4. The pneumoperitoneum apparatus according to claim 1, wherein the gas release is an opening/closing switchable valve.

5. The pneumoperitoneum apparatus according to claim 1, wherein the gas release is provided on the pressure measurement conduit.

6. The pneumoperitoneum apparatus according to claim 1, wherein the gas release is provided on the pressure measurement conduit coupling part.

7. The pneumoperitoneum apparatus according to claim 1, wherein the gas release is included in the relay conduit.

8. The pneumoperitoneum apparatus according to claim 1, wherein the pressure measurement conduit has an inner diameter smaller than an inner diameter of the gas feeding conduit.

9. The pneumoperitoneum apparatus according to claim 1, wherein the controller is configured to control operation of the gas feeding flow rate valve, to control the gas feeding flow rate valve to continuously feed the gas to the body cavity of the patient when a measurement value of the second pressure measurement device is equal to or greater than a predetermined set value, and to control the gas feeding flow rate valve to intermittently feed the gas to the body cavity of the patient when the measurement value of the second pressure measurement section is smaller than the predetermined set value.

10. The pneumoperitoneum apparatus according to claim 1, further comprising:
   an electromagnetic valve provided on the gas feeding conduit, the electromagnetic valve being configured to switch between supplying the gas to the body cavity of the patient and stopping the supply of the gas;
   wherein
   the controller is configured to control the operation of the electromagnetic valve to continuously feed the gas to the body cavity of the patient when a measurement value of the second pressure measurement device is equal to or greater than a predetermined set value, and to control the electromagnetic valve to intermittently feed the gas to the body cavity of the patient when the measurement value of the second pressure measurement device is smaller than the predetermined set value.

11. The pneumoperitoneum apparatus according to claim 1, wherein
   the gas release is an on-off electromagnetic valve configured to be controlled to be on or off by the controller,
   the gas feeding flow rate valve is an electropneumatic proportional valve, and
   the controller is configured to
      bring the electropneumatic proportional valve into an open state and perform continuous gas feeding into the body cavity of the patient through the gas feeding conduit,
      bring the on-off electromagnetic valve into an open state and cause the second pressure measurement device to measure the pressure in the body cavity while the continuous gas feeding is being performed, and
      control the on-off electromagnetic valve to be in a closed state after the measurement of the pressure in the body cavity.

* * * * *